(12) United States Patent
Sapra et al.

(10) Patent No.: US 9,624,482 B2
(45) Date of Patent: Apr. 18, 2017

(54) THERMOPHILIC CELLOBIOHYDROLASE

(75) Inventors: Rajat Sapra, Berkeley, CA (US);
Joshua I. Park, El Cerrito, CA (US);
Supratim Datta, Oakland, CA (US);
Blake A. Simmons, San Francisco, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 12/892,724

(22) Filed: Sep. 28, 2010

(65) Prior Publication Data
US 2011/0207182 A1 Aug. 25, 2011

Related U.S. Application Data

(60) Provisional application No. 61/246,439, filed on Sep. 28, 2009.

(51) Int. Cl.
C12N 9/14 (2006.01)
C12P 19/14 (2006.01)
C12N 9/42 (2006.01)

(52) U.S. Cl.
CPC ............ *C12N 9/2437* (2013.01); *C12P 19/14* (2013.01); *C12Y 302/01091* (2013.01); *C12P 2201/00* (2013.01); *C12P 2203/00* (2013.01)

(58) Field of Classification Search
None
See application file for complete search history.

(56) References Cited

U.S. PATENT DOCUMENTS 6,566,113 B1 5/2003 Takayama et al.

FOREIGN PATENT DOCUMENTS

WO WO 2010/124266 10/2010

OTHER PUBLICATIONS

Hurst et al. Quantitative characterization of substrate-dependent changes in the cellulosome of Clostridium thermocellum, ASMS Conference Aug. 22-28, 2008.*
Blumer-Schuette et al. Extremely thermophilic microorganisms for biomass conversion: status and prospects, Current Opinion in Biotechnology (Jun. 2, 2008), 19: 210-217.*
Xu et al. Assembly and activity of engineered minicellulosomes, BEST Retreat Meeting, Jun. 21-24, 2009.*
Saul et al. celB, a gene coding for a bifunctional cellulase from the extreme thermophile "*Caldocellum saccharolyticum*", Appl and Environ Microbiol (1990), 56(10): 3117-3124.*
Walker et al. Engineering cellulase mixtures by varying the mole fraction of Thermonospora fusca E5 and E3, Trichoderma reesei CBHI and Caldocellum saccharolyticum beta-glucosidase, Biotechnology and Bioengineering (1993), 42: 1019-1028.*
Ando et al, "Hyperthermostable endoglucanase from Pyrococcus horikoshii", Appl Environ Microbiol. Jan. 2002;68 (1):430-3.
Bok et al, "Purification, Characterization, and Molecular Analysis of Thermostable Cellulases CelA and CelB from Thermotoga neapolitana", Appl Environ Microbiol. Dec. 1998; 64(12): 4774-4781.
Bronnenmeier et al, "Purification of Thermotoga maritima enzymes for the degradation of cellulosic materials", Appl Environ Microbiol. Apr. 1995;61(4):1399-407.
Gibbs et al, "Multidomain and Multifunctional Glycosyl Hydrolases from the Extreme Thermophile Caldicellulosiruptor Isolate Tok7B.1", Curr. Microbiol. 2000 40:333-40.
Hermanutz et al, "New Developments in Dissolving and Processing of Cellulose in Ionic Liquids", Macromol. Symp. 2008 262:23-7.
Hreggvidsson et al, "An Extremely Thermostable Cellulase from the Thermophilic Eubacterium Rhodothermus marinus" Appl. Environ. Microbiol. Aug. 1996; 62(8):3047-9.
Kengen et al, "Purification and characterization of an extremely thermostable beta-glucosidase from the hyperthermophilic archaeon Pyrococcus furiosus", Apr. 1993; 213(1):305-12.
Mawadza et al, "Purification and characterization of cellulases produced by two Bacillus strains", J Biotechnol. Oct. 13, 2000;83(3):177-87.
Rainey et al, "Description of *Caldicellulosiruptor saccharolyticus* gen. nov., sp. nov*:* an obligately anaerobic, extremely thermophilic, cellulolytic bacterium", FEMS Microbiol. Lett. 1994; 120:263-6.
Zverlov et al, "Properties and gene structure of a bifunctional cellulolytic enzyme (CelA) from the extreme thermophile '*Anaerocellum thermophilum*' with separate glycosyl hydrolase family 9 and 48 catalytic domains", Microbiology. Feb. 1998;144 ( Pt 2):457-65.

* cited by examiner

*Primary Examiner* — Iqbal H Chowdhury
(74) *Attorney, Agent, or Firm* — Robin C. Chiang; Lawrence Berkeley National Laboratory

(57) ABSTRACT

The present invention provides for a composition comprising a polypeptide comprising a first amino acid sequence having at least 70% identity with the amino acid sequence of Csac GH5 wherein said first amino acid sequence has a thermostable or thermophilic cellobiohydrolase (CBH) or exoglucanase activity.

30 Claims, 5 Drawing Sheets

SEQUENCE LISTING

```
<160> NUMBER OF SEQ ID NOS: 4

<210> SEQ ID NO 1
<211> LENGTH: 3116
<212> TYPE: DNA
<213> ORGANISM: Caldicellulosiruptor saccharolyticus

<400> SEQUENCE: 1
atgaaacgca acctgttccg catcgttagt cgtgtcgtgc tgattgcctt tatcgcgagt      60
attagcctgg tcggtgcaat gtcgtacttc ccggtcgaaa cccaggctgc tcctgactgg     120
tctatcccaa gtctgtgtga gtcctataag gatgatttca tgattggcgt tgcgattccg     180
gcgcgttgcc tgtctaatga cacggacaag cgcatggtgc tgaaacactt taactccatt     240
accgccgaga atgaaatgaa accggaatct ctgctggctg gacagacctc cacgggactg     300
agctaccgtt tctcaaccgc tgatgccttt gttgactttg cttcaaccaa taaaattggc     360
attcgtgggc acactctggt ttggcacaat cagactccag attggttttt tcaaggattc     420
tmtggtcagc gtctgtctaa ggacgctctg ctggcgcgcc tgaaacaata catctatgat     480
gtcgttggac gctacaaagg caaagtctat gcttgggatg ttgttaacga ggcaattgat     540
gagaatcagc cggatagtta ccgtcgctct acctggtatg aaatctgcgg tccggaatat     600
attgaaaagg cgttcatttg ggcgcatgaa gcagacccga acgcgaaact gttttataat     660
gattataaca cggaaattag caaaaaacgc gatttcattt acaacatggt gaaaaatctg     720
aaaagcaaag gcattcctat tcatggcatc ggtatgcagt gtcacattaa tgttaactgg     780
ccgagcgtgt ctgagatcga aaactctatc aaactgttca gctctatccc tgggatcgag     840
attcacatca ccgaactgga catgagcctg tataactacg gctcatctga aaattattca     900
acaccaccgc aggacctgct gcagaaacaa tcacagaaat ataaggaaat ttttaccatg     960
ctgaaaaaat ataaaaacgt ggtgaaatcg gttacctttt ggggtctgaa agacgattat    1020
agctggctgc gttcattta tggtaaaaac gactggccac tgctgttctt cgaggactat    1080
tcggccaaac ctgcgtactg ggcggtcatt gaagcgtcag gcgtgaccac ctcctctcct    1140
actcctaccc cgactccgac cgttacggtc actccaacac cgacccctac gccgacccct    1200
acggtgactg ccactccgac accgacgcca acgcctgttt ctaccccggc gaccggtggc    1260
cagatcaaag tgctgtacgc aaataaagag acgaactcca ctaccaacac aattcgcccg    1320
tggctgaagg tgtcaactcg ggttcatcct caattgatct gagccgtgtc acaatccgct    1380
attggtatac agtggatggt gaacgcgcgc agtctgccgt cagtgactgg gcccagattg    1440
```

```
gtgccagcaa tgtgactttt aaatttgtca agctgagcag tagcgttagc ggcgcggact   1500
attatctgga aattgggttt aagtccggcg cgggccagct gcagccgggg aaggataccg   1560
gcgaaattca aattcgtttc aacaaaagcg actggagtaa ttataatcag gggaacgatt   1620
ggtcctggct gcagagcatg acgagttatg gggaaaacga aaaagtaacc gcttacatcg   1680
acggcgttct ggtgtggggt caggagccaa gtggtgcaac cccggcacca actatgaccg   1740
tagcgccgac tgcaacccct actccgaccc tgtcccctac cgtgacaccg acaccggcac   1800
caacacaaac ggcgattccg acaccgactc tgactccgaa cccgaccccg acctccagca   1860
ttccagatga cacgaatgat gactggctgt atgttagtgg caataaaatc gttgataaag   1920
atggtcgccc ggtttggctg actggtatta actggtttgg gtacaacacc ggtactaacg   1980
tttttgatgg cgtttggtct tgcaacctga agacacccct ggccgagatc gcgaaccgtg   2040
gttttaatct gctgcgcgta cctatctctg cggaactgat cctgaattgg tcgcaaggta   2100
tctacccgaa gccgaatatt aactattatg tgaacccaga gctggagggc aagaacagcc   2160
tggaagtatt cgatattgtt gttcaaacat gcaagaagt aggcctgaaa atcatgctgg    2220
acatccatag tattaaaact gatgcaatgg ccacattta cccagtttgg tatgatgaaa    2280
aattcacccc agaggacttt tacaaagcgt gtgaatggat taccaaccgt tataaaaacg   2340
atgatacgat tattgcgttc gatctgaaaa atgaaccgca tggcaaaccg tgcaagata    2400
ccacattcgc aaagtgggat aattcgacag atattaacaa ctggaaatat gcggccgaaa   2460
cctgcgcaaa acgcatcctg aatattaatc caaacctgct gatcgttatt gaaggaattg   2520
aggcctatcc gaaagatgat gttacctgga cgtctaaatc gagctccgat tactatagca   2580
cttggtgggg tggtaacctg cgtggtgttc gtaaatacc aatcaatctg ggtaaatacc    2640
aaaacaaagt agtttattcg cctcatgact atggcccgag cgtgtatcag caaccgtggt   2700
tttaccctgg ttttacaaaa gagagcctgc tgcaggattg ctggcgtcca aattgggcgt   2760
acatcatgga ggaaaacatc gcaccgctgc tgatcggcga atggggtggg cacctggacg   2820
gtgcggataa tgaaaagtgg atgaaatacc tgcgtgacta cattatcgaa accacatcc   2880
atcatacgtt ttggtgcttt aacgcaaatt ccggcgatac gggggggtctg gtaggttacg   2940
attttacaac atgggatgag aaaaagtata gtttttctgaa accggctctg tggcaggaca   3000
gccagggtcg tttcgtgggt ctggatcata acgcccgct ggggacaaat ggtaaaaata    3060
tcaatattac tacctactac aacaataacg agccggaacc ggtcccggca tctaaa        3116
```

<210> SEQ ID NO 2
<211> LENGTH: 1039
<212> TYPE: PRT
<213> ORGANISM: Caldicellulosiruptor saccharolyticus

<400> SEQUENCE: 2

```
Met Lys Arg Asn Leu Phe Arg Ile Val Ser Arg Val Val Leu Ile Ala
1               5                   10                  15

Phe Ile Ala Ser Ile Ser Leu Val Gly Ala Met Ser Tyr Phe Pro Val
            20                  25                  30

Glu Thr Gln Ala Ala Pro Asp Trp Ser Ile Pro Ser Leu Cys Glu Ser
        35                  40                  45

Tyr Lys Asp Asp Phe Met Ile Gly Val Ala Ile Pro Ala Arg Cys Leu
    50                  55                  60

Ser Asn Asp Thr Asp Lys Arg Met Val Leu Lys His Phe Asn Ser Ile
65                  70                  75                  80
```

```
Thr Ala Glu Asn Glu Met Lys Pro Glu Ser Leu Leu Ala Gly Gln Thr
                    85                  90                  95
Ser Thr Gly Leu Ser Tyr Arg Phe Ser Thr Ala Asp Ala Phe Val Asp
                100                 105                 110
Phe Ala Ser Thr Asn Lys Ile Gly Ile Arg Gly His Thr Leu Val Trp
                115                 120                 125
His Asn Gln Thr Pro Asp Trp Phe Phe Lys Asp Ser Asn Gly Gln Arg
130                 135                 140
Leu Ser Lys Asp Ala Leu Leu Ala Arg Leu Lys Gln Tyr Ile Tyr Asp
145                 150                 155                 160
Val Val Gly Arg Tyr Lys Gly Lys Val Tyr Ala Trp Asp Val Val Asn
                165                 170                 175
Glu Ala Ile Asp Glu Asn Gln Pro Asp Ser Tyr Arg Arg Ser Thr Trp
                180                 185                 190
Tyr Glu Ile Cys Gly Pro Glu Tyr Ile Glu Lys Ala Phe Ile Trp Ala
                195                 200                 205
His Glu Ala Asp Pro Asn Ala Lys Leu Phe Tyr Asn Asp Tyr Asn Thr
210                 215                 220
Glu Ile Ser Lys Lys Arg Asp Phe Ile Tyr Asn Met Val Lys Asn Leu
225                 230                 235                 240
Lys Ser Lys Gly Ile Pro Ile His Gly Ile Gly Met Gln Cys His Ile
                245                 250                 255
Asn Val Asn Trp Pro Ser Val Ser Glu Ile Glu Asn Ser Ile Lys Leu
                260                 265                 270
Phe Ser Ile Pro Gly Ile Glu Ile His Ile Thr Glu Leu Asp Met
                275                 280                 285
Ser Leu Tyr Asn Tyr Gly Ser Ser Glu Asn Tyr Ser Thr Pro Pro Gln
290                 295                 300
Asp Leu Leu Gln Lys Gln Ser Gln Lys Tyr Lys Glu Ile Phe Thr Met
305                 310                 315                 320
Leu Lys Lys Tyr Lys Asn Val Val Lys Ser Val Thr Phe Trp Gly Leu
                325                 330                 335
Lys Asp Asp Tyr Ser Trp Leu Arg Ser Phe Tyr Gly Lys Asn Asp Trp
                340                 345                 350
Pro Leu Leu Phe Phe Glu Asp Tyr Ser Ala Lys Pro Ala Tyr Trp Ala
                355                 360                 365
Val Leu Glu Ala Ser Gly Val Thr Thr Ser Ser Pro Thr Pro Thr Pro
                370                 375                 380
Thr Pro Thr Val Thr Val Thr Pro Thr Pro Thr Pro Thr Pro Thr Pro
385                 390                 395                 400
Thr Val Thr Ala Thr Pro Thr Pro Thr Pro Val Ser Thr Pro
                    405                 410                 415
Ala Thr Gly Gly Gln Ile Lys Val Leu Tyr Ala Asn Lys Glu Thr Asn
                420                 425                 430
Ser Thr Thr Asn Thr Ile Arg Pro Trp Leu Lys Val Asn Ser Gly
                435                 440                 445
Ser Ser Ser Ile Asp Leu Ser Arg Val Thr Ile Arg Tyr Trp Tyr Thr
                450                 455                 460
Val Asp Gly Glu Arg Ala Gln Ser Ala Val Ser Asp Trp Ala Gln Ile
465                 470                 475                 480
Gly Ala Ser Asn Val Thr Phe Lys Phe Val Lys Leu Ser Ser Val
                485                 490                 495
```

-continued

Ser Gly Ala Asp Tyr Tyr Leu Glu Ile Gly Phe Lys Ser Gly Ala Gly
            500                 505                 510

Gln Leu Gln Pro Gly Lys Asp Thr Gly Glu Ile Gln Ile Arg Phe Asn
            515                 520                 525

Lys Ser Asp Trp Ser Asn Tyr Asn Gln Gly Asn Asp Trp Ser Trp Leu
        530                 535                 540

Gln Ser Met Thr Ser Tyr Gly Glu Asn Glu Lys Val Thr Ala Tyr Ile
545                 550                 555                 560

Asp Gly Val Leu Val Trp Gly Gln Glu Pro Ser Gly Ala Thr Pro Ala
            565                 570                 575

Pro Thr Met Thr Val Ala Pro Thr Ala Thr Pro Thr Pro Thr Leu Ser
            580                 585                 590

Pro Thr Val Thr Pro Thr Pro Ala Pro Thr Gln Thr Ala Ile Pro Thr
            595                 600                 605

Pro Thr Leu Thr Pro Asn Pro Thr Pro Thr Ser Ser Ile Pro Asp Asp
            610                 615                 620

Thr Asn Asp Asp Trp Leu Tyr Val Ser Gly Asn Lys Ile Val Asp Lys
625                 630                 635                 640

Asp Gly Arg Pro Val Trp Leu Thr Gly Ile Asn Trp Phe Gly Tyr Asn
            645                 650                 655

Thr Gly Thr Asn Val Phe Asp Gly Val Trp Ser Cys Asn Leu Lys Asp
            660                 665                 670

Thr Leu Ala Glu Ile Ala Asn Arg Gly Phe Asn Leu Leu Arg Val Pro
            675                 680                 685

Ile Ser Ala Glu Leu Ile Leu Asn Trp Ser Gln Gly Ile Tyr Pro Lys
            690                 695                 700

Pro Asn Ile Asn Tyr Tyr Val Asn Pro Glu Leu Glu Gly Lys Asn Ser
705                 710                 715                 720

Leu Glu Val Phe Asp Ile Val Val Gln Thr Cys Lys Glu Val Gly Leu
            725                 730                 735

Lys Ile Met Leu Asp Ile His Ser Ile Lys Thr Asp Ala Met Gly His
            740                 745                 750

Ile Tyr Pro Val Trp Tyr Asp Glu Lys Phe Thr Pro Glu Asp Phe Tyr
            755                 760                 765

Lys Ala Cys Glu Trp Ile Thr Asn Arg Tyr Lys Asn Asp Asp Thr Ile
            770                 775                 780

Ile Ala Phe Asp Leu Lys Asn Glu Pro His Gly Lys Pro Trp Gln Asp
785                 790                 795                 800

Thr Thr Phe Ala Lys Trp Asp Asn Ser Thr Asp Ile Asn Asn Trp Lys
            805                 810                 815

Tyr Ala Ala Glu Thr Cys Ala Lys Arg Ile Leu Asn Ile Asn Phe Asn
            820                 825                 830

Leu Leu Ile Val Ile Glu Gly Ile Glu Ala Tyr Pro Lys Asp Asp Val
            835                 840                 845

Thr Trp Thr Ser Lys Ser Ser Asp Tyr Tyr Ser Thr Trp Trp Gly
            850                 855                 860

Gly Asn Leu Arg Gly Val Arg Lys Tyr Pro Ile Asn Leu Gly Lys Tyr
865                 870                 875                 880

Gln Asn Lys Val Val Tyr Ser Pro His Asp Tyr Gly Pro Ser Val Tyr
            885                 890                 895

Gln Gln Pro Trp Phe Tyr Pro Gly Phe Thr Lys Glu Ser Leu Leu Gln
            900                 905                 910

Asp Cys Trp Arg Pro Asn Trp Ala Tyr Ile Met Glu Glu Asn Ile Ala

```
                    915                 920                 925
Pro Leu Leu Ile Gly Glu Trp Gly Gly His Leu Asp Gly Ala Asp Asn
    930                 935                 940

Glu Lys Trp Met Lys Tyr Leu Arg Asp Tyr Ile Ile Glu Asn His Ile
945                 950                 955                 960

His His Thr Phe Trp Cys Phe Asn Ala Asn Ser Gly Asp Thr Gly Gly
                965                 970                 975

Leu Val Gly Tyr Asp Phe Thr Thr Trp Asp Glu Lys Tyr Ser Phe
            980                 985                 990

Leu Lys Pro Ala Leu Trp Gln Asp Ser Gln Gly Arg Phe Val Gly Leu
            995                 1000                1005

Asp His Lys Arg Pro Leu Gly Thr Asn Gly Lys Asn Ile Asn Ile
    1010                1015                1020

Thr Thr Tyr Tyr Asn Asn Glu Pro Glu Pro Val Pro Ala Ser
    1025                1030                1035

Lys

<210> SEQ ID NO 3
<211> LENGTH: 534
<212> TYPE: PRT
<213> ORGANISM: Caldicellulosiruptor saccharolyticus

<400> SEQUENCE: 3

Met Phe Lys Ser Gly Ala Gly Gln Leu Gln Pro Gly Lys Asp Thr Gly
1               5                   10                  15

Glu Ile Gln Ile Arg Phe Asn Lys Ser Asp Trp Ser Asn Tyr Asn Gln
            20                  25                  30

Gly Asn Asp Trp Ser Trp Leu Gln Ser Met Thr Ser Tyr Gly Glu Asn
        35                  40                  45

Glu Lys Val Thr Ala Tyr Ile Asp Gly Val Leu Val Trp Gly Gln Glu
    50                  55                  60

Pro Ser Gly Ala Thr Pro Ala Pro Thr Met Thr Val Ala Pro Thr Ala
65                  70                  75                  80

Thr Pro Thr Pro Thr Leu Ser Pro Thr Val Thr Pro Thr Pro Ala Pro
                85                  90                  95

Thr Gln Thr Ala Ile Pro Thr Pro Thr Leu Thr Pro Asn Pro Thr Pro
            100                 105                 110

Thr Ser Ser Ile Pro Asp Asp Thr Asn Asp Asp Trp Leu Tyr Val Ser
        115                 120                 125

Gly Asn Lys Ile Val Asp Lys Asp Gly Arg Pro Val Trp Leu Thr Gly
    130                 135                 140

Ile Asn Trp Phe Gly Tyr Asn Thr Gly Thr Asn Val Phe Asp Gly Val
145                 150                 155                 160

Trp Ser Cys Asn Leu Lys Asp Thr Leu Ala Glu Ile Ala Asn Arg Gly
                165                 170                 175

Phe Asn Leu Leu Arg Val Pro Ile Ser Ala Glu Leu Ile Leu Asn Trp
            180                 185                 190

Ser Gln Gly Ile Tyr Pro Lys Pro Asn Ile Asn Tyr Val Asn Pro
        195                 200                 205

Glu Leu Glu Gly Lys Asn Ser Leu Glu Val Phe Asp Ile Val Val Gln
    210                 215                 220

Thr Cys Lys Glu Val Gly Leu Lys Ile Met Leu Asp Ile His Ser Ile
225                 230                 235                 240

Lys Thr Asp Ala Met Gly His Ile Tyr Pro Val Trp Tyr Asp Glu Lys
```

```
                    245                 250                 255
Phe Thr Pro Glu Asp Phe Tyr Lys Ala Cys Glu Trp Ile Thr Asn Arg
            260                 265                 270

Tyr Lys Asn Asp Asp Thr Ile Ile Ala Phe Asp Leu Lys Asn Glu Pro
        275                 280                 285

His Gly Lys Pro Trp Gln Asp Thr Thr Phe Ala Lys Trp Asp Asn Ser
    290                 295                 300

Thr Asp Ile Asn Asn Trp Lys Tyr Ala Ala Glu Thr Cys Ala Lys Arg
305                 310                 315                 320

Ile Leu Asn Ile Asn Pro Asn Leu Leu Ile Val Ile Glu Gly Leu Glu
                325                 330                 335

Ala Tyr Pro Lys Asp Asp Val Thr Trp Thr Ser Lys Ser Ser Ser Asp
            340                 345                 350

Tyr Tyr Ser Thr Trp Trp Gly Gly Asn Leu Arg Gly Val Arg Lys Tyr
        355                 360                 365

Pro Ile Asn Leu Gly Lys Tyr Gln Asn Lys Val Val Tyr Ser Pro His
    370                 375                 380

Asp Tyr Gly Pro Ser Val Tyr Gln Gln Pro Trp Phe Tyr Pro Gly Phe
385                 390                 395                 400

Thr Lys Glu Ser Leu Leu Gln Asp Cys Trp Arg Pro Asn Trp Ala Tyr
                405                 410                 415

Leu Met Glu Glu Asn Ile Ala Pro Leu Leu Ile Gly Trp Gly Gly
            420                 425                 430

His Leu Asp Gly Ala Asp Asn Glu Lys Trp Met Lys Tyr Leu Arg Asp
        435                 440                 445

Tyr Ile Ile Glu Asn His Ile His His Thr Phe Trp Cys Phe Asn Ala
    450                 455                 460

Asn Ser Gly Asp Thr Gly Gly Leu Val Gly Tyr Asp Phe Thr Thr Trp
465                 470                 475                 480

Asp Glu Lys Lys Tyr Ser Phe Leu Lys Pro Ala Leu Trp Gln Asp Ser
                485                 490                 495

Gln Gly Arg Phe Val Gly Leu Asp His Lys Arg Pro Leu Gly Thr Asn
            500                 505                 510

Gly Lys Asn Ile Asn Ile Thr Thr Tyr Tyr Asn Asn Asn Glu Pro Glu
        515                 520                 525

Pro Val Pro Ala Ser Lys
    530

<210> SEQ ID NO 4
<211> LENGTH: 666
<212> TYPE: PRT
<213> ORGANISM: Caldicellulosiruptor saccharolyticus

<400> SEQUENCE: 4

Met Gly Val Thr Thr Ser Ser Pro Thr Pro Thr Pro Thr Pro Thr Val
1               5                   10                  15

Thr Val Thr Pro Thr Pro Thr Pro Thr Pro Thr Pro Thr Val Thr Ala
            20                  25                  30

Thr Pro Thr Pro Thr Pro Thr Pro Val Ser Thr Pro Ala Thr Gly Gly
        35                  40                  45

Gln Ile Lys Val Leu Tyr Ala Asn Lys Glu Thr Asn Ser Thr Thr Asn
    50                  55                  60

Thr Ile Arg Pro Trp Leu Lys Val Val Asn Ser Gly Ser Ser Ser Ile
65                  70                  75                  80
```

```
Asp Leu Ser Arg Val Thr Ile Arg Tyr Trp Tyr Thr Val Asp Gly Glu
                85                  90                  95
Arg Ala Gln Ser Ala Val Ser Asp Trp Ala Gln Ile Gly Ala Ser Asn
            100                 105                 110
Val Thr Phe Lys Phe Val Lys Leu Ser Ser Val Ser Gly Ala Asp
            115                 120                 125
Tyr Tyr Leu Glu Ile Gly Phe Lys Ser Gly Ala Gly Gln Leu Gln Pro
            130                 135                 140
Gly Lys Asp Thr Gly Glu Ile Gln Ile Arg Phe Asn Lys Ser Asp Trp
145                 150                 155                 160
Ser Asn Tyr Asn Gln Gly Asn Asp Trp Ser Trp Leu Gln Ser Met Thr
                165                 170                 175
Ser Tyr Gly Glu Asn Glu Lys Val Thr Ala Tyr Ile Asp Gly Val Leu
            180                 185                 190
Val Trp Gly Gln Glu Pro Ser Gly Ala Thr Pro Ala Pro Thr Met Thr
            195                 200                 205
Val Ala Pro Thr Ala Thr Pro Thr Pro Thr Leu Ser Pro Thr Val Thr
    210                 215                 220
Pro Thr Pro Ala Pro Thr Gln Thr Ala Ile Pro Thr Pro Thr Leu Thr
225                 230                 235                 240
Pro Asn Pro Thr Pro Thr Ser Ser Ile Pro Asp Asp Thr Asn Asp Asp
                245                 250                 255
Trp Leu Tyr Val Ser Gly Asn Lys Ile Val Asp Lys Asp Gly Arg Pro
                260                 265                 270
Val Trp Leu Thr Gly Ile Asn Trp Phe Gly Tyr Asn Thr Gly Thr Asn
            275                 280                 285
Val Phe Asp Gly Val Trp Ser Cys Asn Leu Lys Asp Thr Leu Ala Glu
            290                 295                 300
Ile Ala Asn Arg Gly Phe Asn Leu Leu Arg Val Pro Ile Ser Ala Glu
305                 310                 315                 320
Leu Ile Leu Asn Trp Ser Gln Gly Ile Tyr Pro Lys Pro Asn Ile Asn
                325                 330                 335
Tyr Tyr Val Asn Pro Glu Leu Glu Gly Lys Asn Ser Leu Glu Val Phe
                340                 345                 350
Asp Ile Val Val Gln Thr Cys Lys Glu Val Gly Leu Lys Ile Met Leu
            355                 360                 365
Asp Ile His Ser Ile Lys Thr Asp Ala Met Gly His Ile Tyr Pro Val
            370                 375                 380
Trp Tyr Asp Glu Lys Phe Thr Pro Glu Asp Phe Tyr Lys Ala Cys Glu
385                 390                 395                 400
Trp Ile Thr Asn Arg Tyr Lys Asn Asp Asp Thr Ile Ile Ala Phe Asp
                405                 410                 415
Leu Lys Asn Glu Pro His Gly Lys Pro Trp Gln Asp Thr Thr Phe Ala
            420                 425                 430
Lys Trp Asp Asn Ser Thr Asp Ile Asn Asn Trp Lys Tyr Ala Ala Glu
            435                 440                 445
Thr Cys Ala Lys Arg Ile Leu Asn Ile Asn Pro Asn Leu Leu Ile Val
    450                 455                 460
Ile Glu Gly Leu Glu Ala Tyr Pro Lys Asp Asp Val Thr Trp Thr Ser
465                 470                 475                 480
Lys Ser Ser Ser Asp Tyr Val Ser Thr Trp Trp Gly Gly Asn Leu Arg
                485                 490                 495
Gly Val Arg Lys Tyr Pro Ile Asn Leu Gly Lys Tyr Gln Asn Lys Val
```

-continued

```
                500                 505                 510
Val Tyr Ser Pro His Asp Tyr Gly Pro Ser Val Tyr Gln Gln Pro Trp
        515                 520                 525

Phe Tyr Pro Gly Phe Thr Lys Glu Leu Leu Gln Asp Cys Trp Arg Pro
        530                 535                 540

Asn Trp Ala Tyr Leu Met Glu Glu Asn Ile Ala Pro Leu Leu Ile Gly
545                 550                 555                 560

Glu Trp Gly Gly His Leu Asp Gly Ala Asp Asn Glu Lys Trp Met Lys
                565                 570                 575

Tyr Leu Arg Asp Tyr Ile Ile Glu Asn His Ile His His Thr Phe Trp
            580                 585                 590

Cys Phe Asn Ala Asn Ser Gly Asp Thr Gly Gly Leu Val Gly Tyr Asp
        595                 600                 605

Phe Thr Thr Trp Asp Glu Lys Lys Tyr Ser Phe Leu Lys Pro Ala Leu
        610                 615                 620

Trp Gln Asp Ser Gln Gly Arg Phe Val Gly Leu Asp His Lys Arg Pro
625                 630                 635                 640

Leu Gly Thr Asn Gly Lys Asn Ile Asn Ile Thr Thr Tyr Tyr Asn Asn
                645                 650                 655

Asn Glu Pro Glu Pro Val Pro Ala Ser Lys
                660                 665
```

THERMOPHILIC CELLOBIOHYDROLASE

CROSS-REFERENCE TO RELATED APPLICATIONS

This application claims priority to U.S. Provisional Patent Application Ser. No. 61/246,439, filed Sep. 28, 2009, hereby incorporated by reference.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of saccharification of biomass.

BACKGROUND OF THE INVENTION

Ionic liquid pretreatment method has been used to convert lignocellulose to sugars, since current pretreatment approaches are energy and cost intensive. Methods are being developed for the conversion of crystalline cellulose to sugars with improvements in yield and rate of sugar production using a simultaneous pretreatment and saccharification using a one step ionic liquid. The pretreatment step has been developed with the use of ionic liquid to break down crystalline cellulosic biomass. While the second step of hydrolyzing cellulose to sugars would require separation of cellulose from ionic liquid, an enzyme that is compatible with the concentrations of ionic liquid used in pretreatment step would eliminate the need for this step, thereby improving yield and reducing time and cost.

Currently, people use techniques that are based on treating the biomass with a combination of high temperature and acid or base, or chemicals like lime. These methods have two distinct disadvantages: first, the industrial enzymes are used to break down cellulose are not compatible with such harsh methods making a single pretreatment and saccharification method impossible. Secondly, these methods create unwanted byproducts that interfere with the downstream hydrolysis and fuel production steps.

SUMMARY OF THE INVENTION

The present invention provides for a composition comprising a polypeptide comprising a first amino acid sequence having at least 70% identity with the amino acid sequence of Csac GH5 wherein said first amino acid sequence has a thermostable or thermophilic cellobiohydrolase (CBH) or exoglucanase activity. In some embodiments, the polypeptide further comprises a second amino acid sequence having at least 70% identity with the amino acid sequence of Csac CBM3 wherein said second amino acid sequence is capable of binding a carbohydrate. In some embodiments, the carbohydrate is a cellulose. In some embodiments, the composition further comprises a cellulose capable of being cleaved by the Csac GH5 to produce a cellobiose. In some embodiments, the composition comprises a biomass comprising a cellulose capable of being cleaved by the Csac GH5 to produce a cellobiose. In some embodiments, the composition has a temperature of at least 65° C. In some embodiments, the composition has a pH from 4.7 to 5.5. In some embodiments of the invention, the composition further comprises one or more endoglucanase enzymes. In some embodiments, the composition further comprises a suitable ionic liquid (IL). The suitable IL used in the present invention can be any IL suitable for pretreatment of biomass and for the hydrolysis of cellulose by a thermostable cellulase. In some embodiments, the composition further comprises a cellobiose produced by the cleavage of a cellulose in the composition by the polypeptide.

The present invention provides for a nucleic acid encoding the polypeptide of the present invention, wherein the polypeptide comprises a first amino acid sequence having at least 70% identity with the amino acid sequence of Csac GH5 wherein said first amino acid sequence has a thermostable or thermophilic cellobiohydrolase (CBH) or exoglucanase activity, and optionally a second amino acid sequence having at least 70% identity with the amino acid sequence of Csac CBM3 wherein said second amino acid sequence is capable of binding a carbohydrate. In some embodiments of the invention, the nucleic acid is recombinant and/or isolated or purified.

The present invention provides for a composition comprising an ionic liquid and a polypeptide comprising the amino acid sequence of Csac GH5 and having a CBH or exoglucanase activity. In some embodiments, the composition further comprises a cellulose, wherein the polypeptide is capable of hydrolyzing the cellulose. In some embodiments, the composition comprises a pretreatment biomass.

The present invention provides for a method of hydrolyzing a cellulose, comprising: (a) providing a composition comprising a solution comprising an ionic liquid (IL) and a cellulose, and (b) introducing a polypeptide comprising the amino acid sequence of Csac GH5 and having a CBH or exoglucanase activity to the solution, such that the cellulose is hydrolyzed by the polypeptide. In some embodiments, the solution comprises a pretreatment biomass.

In some embodiments, the pretreatment biomass is a pretreatment cellulose biomass, pretreatment hemicellulose biomass, pretreatment lingo-cellulose biomass, or a mixture thereof.

The present invention provides for a method for converting lignocellulosic biomass to sugars for the production of biofuels. Methods for the pretreatment of biomass and the downstream enzymatic hydrolysis that is required to breakdown the long polymers of cellulose to simpler sugars for biofuels production.

The present invention provides for a method that is compatible with biomass pretreatment with IL.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
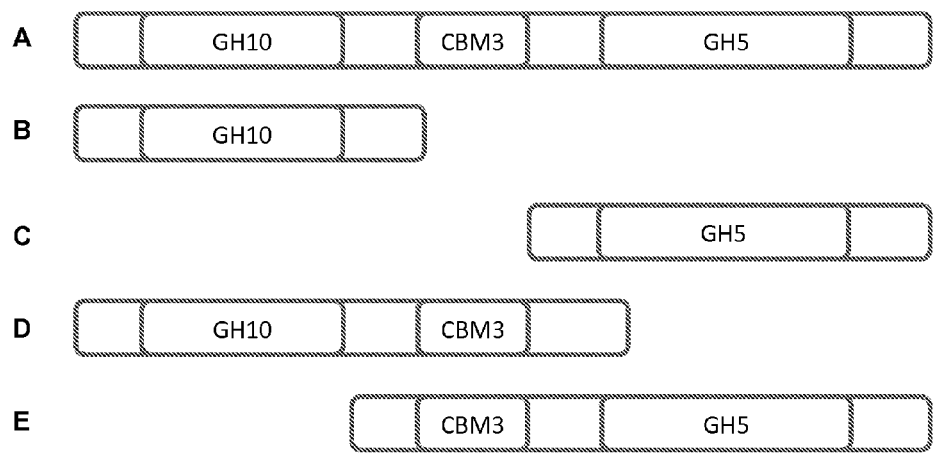
FIG. 1 shows the constructs constructed and tested in Example 1. Construct A contains amino acids 37-1039. Construct B contains amino acids 37-423. Construct C contains amino acids 507-1039. Construct D contains amino acids 37-635. Construct E contains amino acids 374-1039.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Thermostable Cellulase from *Caldicellulosiruptor saccharolyticus*

The present invention provides for a composition comprising a polypeptide comprising a first amino acid sequence having at least 70% identity with the amino acid sequence of Csac GH5 wherein said first amino acid sequence has a thermostable or thermophilic cellobiohydrolase (CBH) or exoglucanase activity. In some embodiments, the polypeptide further comprises a second amino acid sequence having at least 70% identity with the amino acid sequence of Csac CBM3 wherein said second amino acid sequence is capable of binding a carbohydrate. In some embodiments, the carbohydrate is a cellulose. In some embodiments, the composition further comprises a cellulose capable of being cleaved by the Csac GH5 to produce a cellobiose. In some embodiments, the composition comprises a biomass comprising a cellulose capable of being cleaved by the Csac GH5 to produce a cellobiose. In some embodiments, the composition has a temperature of at least 65° C. In some embodiments, the composition has a pH from 4.7 to 5.5.

The YP_001179883 gene of *Caldicellulosiruptor saccharolyticus* ("Csac") encodes the CBH protein which encompasses the glycoside hydrolase family-5 domain (GH5) which is a cellobiohydrolase (EC 3.2.1.91; UniProt ID A4XIF7) that can break down cellulose into cellobiose at high temperatures. The CBH protein comprises the 3 distinct functional domains: GH10, CBM3, and GH5. The CBH protein can be used for the hydrolysis of cellulosic sugars to cellobiose and glucose. The CBH protein is compatible with IL pretreatment. The CBH protein substantially improves the yield of saccharification of cellulose compared to commercially available enzymes and is active in the presence of up to about 50% 1-ethyl-3-methylimidazolium (EMIN) acetate. The CBH protein is optimally active at about 80° C. and from pH 4.7 to pH 5.5.

The Csac GH5 domain has cellulase activity against both soluble and crystalline cellulose to produce oligosaccharides of glucose. The GH5 domain from Csac CBH is a novel hyperthermophilic CBH, and only the second CBH identified from hyperthermophiles. The enzymatic activity of the protein is characterized and found that the optimal cellobiohydrolase activity is observed at pH 4.7-5.5 at 80° C. The enzyme can catalyze the model solute substrate 4-nitrophenyl β-D-cellobioside with a $V_{max}$ of 0.71 μmol/min/mg and a $K_m$ of 2.2 mM at 80° C. in 50 mM MES at pH 5.5. The product inhibition of cellobiose is determined under the optimal condition of the enzyme activity, with $IC_{50}$ of ca. 30 mM. At least 80% of CBH activity is retained with 2.3 M NaCl with a carbohydrate binding module-3 domain. The GH5 of Csac can produce both cellobiose and glucose from both pretreated ad untreated Avicel after 17 hours incubation at 80° C. These results demonstrate that GH5 from Csac is a hyperthermophilic CBH that can degrade both soluble and microcystalline substrates. In addition, the protein is tolerant and active in very high concentrations of IL, such as EMIM Acetate. There is no loss of activity of GH5 in concentration up to 20% IL and the activity actually slightly increases in concentrations of up to 20% IL. The enzyme is tolerant of concentrations of IL up to 50% by volume.

In some embodiments of the invention, the first amino acid sequence has at least 80% identity with the amino acid sequence of Csac GH5. In some embodiments of the invention, the first amino acid sequence has at least 90% identity with the amino acid sequence of Csac GH5. In some embodiments of the invention, the first amino acid sequence has at least 95% identity with the amino acid sequence of Csac GH5. In some embodiments of the invention, the first amino acid sequence has at least 99% identity with the amino acid sequence of Csac GH5. In some embodiments of the invention, the Csac GH5 comprises the amino acid sequence of SEQ ID NO:3. The Csac GH5 comprises the amino acid sequence of amino acids 636-975 of Csac CBH.

In some embodiments of the invention, the second amino acid sequence has at least 80% identity with the amino acid sequence of Csac CBM3. In some embodiments of the invention, the second amino acid sequence has at least 90% identity with the amino acid sequence of Csac CBM3. In some embodiments of the invention, the second amino acid sequence has at least 95% identity with the amino acid sequence of Csac CBM3. In some embodiments of the invention, the second amino acid sequence has at least 99% identity with the amino acid sequence of Csac CBM3. The Csac CBM3 comprises the amino acid sequence of amino acids 424-506 of Csac CBH.

The following is a nucleotide sequence comprising a codon optimized nucleotide sequence encoding Csac CBH (SEQ ID NO:1):

```
ATGAAACGCAACCTGTTCCGCATCGTTAGTCGTGTCGTGCTGATTGCCTTTATCGCGAGT-
ATTAGCCTGGTCGGTGCAATGTCGTACTT

CGGCCTCGAAACCCAGGCTGCTCCTGACTGGTCTATCCCAAGTCTGTGTGAGTC-
CTATAAGGATGATTTCATGATTGGCGTTGCGATTC

CGGCGCGTTGCCTGTCTAATGACACGGACAAGCGCATGGTGCTGAAACACTTTAACTC-
CATTACCGCCGAGAATGAAATGAAACCGGAA

TCTCTGCTGGCTGGACAGACCTCCACGGGACTGAGCTACCGTTTCTCAACCGCTGATGC-
CTTTGTTGACTTTGCTTCAACCAATAAAAT

TGGCATTCGTGGGCACACTCTGGTTTGGCACAATCAGACTCCAGATTG-
GTTTTTCAAGGATTCTAATGGTCAGCGTCTGTCTAAGGACG

CTCTGCTGGCGCGCCTGAAACAATACATCTATGATGTCGTTGGACGCTA-
CAAAGGCAAAGTCTATGCTTGGGATGTTGTTAACGAGGCA

ATTGATGAGAATCAGCCGGATAGTTACCGTCGCTCTACCTGGTATGAAATCTGCGGTCCG-
GAATATATTGAAAAGGCGTTCATTTGGGC

GCATGAAGCAGACCCGAACGCGAAACTGTTTTATAATGATTATAACACGGAAATTAG-
CAAAAAACGCGATTTCATTTACAACATGGTGA

AAAATCTGAAAAGCAAAGGCATTCCTATTCATGGCATCGGTATGCAGTGTCACATTAAT-
GTTAACTGGCCGAGCGTGTCTGAGATCGAA

AACTCTATCAAACTGTTCAGCTCTATCCCTGGGATCGAGATTCACATCACCGAACTGGA-
CATGAGCCTGTATAACTACGGCTCATCTGA

AAATTATTCAACACCACCGCAGGACCTGCTGCAGAAACAATCACA-
GAAATATAAGGAAATTTTTACCATGCTGAAAAAATATAAAAACG

TGGTGAAATCGGTTACCTTTTGGGGTCTGAAAGACGATTATAGCTGGCTGCGTTCATTT-
TATGGTAAAAACGACTGGCCACTGCTGTTC

TTCGAGGACTATTCGGCCAAACCTGCGTACTGGGCGGTCATTGAAGCGTCAGGCGTGAC-
CACCTCCTCTCCTACTCCTACCCCGACTCC

GACCGTTACGGTCACTCCAACACCGACCCCTACGCCGACCCCTACGGTGACTGCCACTC-
CGACACCGACGCCAACGCCTGTTTCTACCC

CGGCGACCGGTGGCCAGATCAAAGTGCTGTACGCAAATAAAGAGACGAACTCCACTAC-
CAACACAATTCGCCCCGTGGTGAAGGTGGTC

AACTCGGGTTCATCCTCAATTGATCTGAGCCGTGTCACAATCCGCTATTGGTATACAGTG-
GATGGTGAACGCGCGCAGTCTGCCGTCAG

TGACTGGGCCCAGATTGGTGCCAGCAATGTGACTTTTAAATTTGTCAAGCTGAGCAG-
TAGCGTTAGCGGCGCGGACTATTATCTGGAAA

TTGGGTTTAAGTCCGGCGCGGGCCAGCTGCAGCCGGGGAAGGATACCGGCGAAAT-
TCAAATTCGTTTCAACAAAAGCGACTGGAGTAAT

TATAATCAGGGGAACGATTGGTCCTGGCTGCAGAGCATGACGAGTTATGGGGAAAAC-
GAAAAAGTAACCGCTTACATCGACGGCGTTCT

GGTGTGGGGTCAGGAGCCAAGTGGTGCAACCCCGGCACCAACTATGACCGTAGCGC-
CGACTGCAACCCCTACTCCGACCCTGTCCCCTA

CCGTGACACCGACACCGGCACCAACACAAACGGCGATTCCGACACCGACTCTGACTC-
CGAACCCGACCCCGACCTCCAGCATTCCAGAT

GACACGAATGATGACTGGCTGTATGTTAGTGGCATAAAATCGTTGATAAAGATGGTCGCCCGGTTTGGCTGACTGGTATTAACTGGTT

TGGGTACAACACCGGTACTAACGTTTTGATGGCGTTTGGTCTTGCAACCTGAAAGACAC-
CCTGGCCGAGATCGCGAACCGTGGTTTTA

ATCTGCTGCGCGTACCTATCTCTGCGGAACTGATCCTGAATTGGTCGCAAGGTATCTAC-
CCGAAGCCGAATATTAACTATTATGTGAAC

CCAGAGCTGGAGGGCAAGAACAGCCTGGAAGTATTCGATATTGTTGTTCAAACATG-
CAAAGAAGTAGGCCTGAAAATCATGCTGGACAT

CCATAGTATTAAAACTGATGCAATGGGCCACATTTACCCAGTTTGGTATGATGAAAAT-
TCACCCCAGAGGACTTTTACAAAGCGTGTG

AATGGATTACCAACCGTTATAAAAACGATGATACGATTATTGCGTTCGATCTGAAAAAT-
GAACCGCATGGCAAACCGTGGCAAGATACC
```

-continued
ACATTCGCAAAGTGGGATAATTCGACAGATATTAACAACTGGAAATATGCGGCCGAAAC
CTGCGCAAAACGCATCCTGAATATTAATCC AAACCTGCTGATCGTTATTGAAGGAATTGAGGCCTATCCGAAAGATGATGTTACCTG
GACGTCTAAATCGAGCTCCGATTACTATAGCA CTTGGTGGGGTGGTAACCTGCGTGGTGTTCGTAAATACCCAATCAATCTGGGTAAATAC
CAAAACAAAGTAGTTTATTCGCCTCATGAC TATGGCCCGAGCGTGTATCAGCAACCGTGGTTTTACCCTGGTTTTACAAAAGAGAGCCT
GCTGCAGGATTGCTGGCGTCCAAATTGGGC GTACATCATGGAGGAAAACATCGCACCGCTGCTGATCGGCGAATGGGGTGGGCACCTG
GACGGTGCGGATAATGAAAAGTGGATGAAAT ACCTGCGTGACTACATTATCGAAAACCACATCCATCATACGTTTTGGTGCTTTAACG
CAAATTCCGGCGATACGGGGGGTCTGGTAGGT TACGATTTTACAACATGGGATGAGAAAAAGTATAGTTTTCTGAAACCGGCTCTGTGGCAG
GACAGCCAGGGTCGTTTCGTGGGTCTGGA TCATAAACGCCCGCTGGGGACAAATGGTAAAAATATCAATATTACTACCTACTA
CAACAATAACGAGCCGGAACCGGTCCCGGCATCTA

AA

The following is the amino acid sequence (aa 1-1039) of Csac CBH (SEQ ID NO:2):

MKRNLFRIVSRVVLIAFIASISLVGAMSYFPVETQAAPDWSIPSLCESYKDDPMIGVAIPARCLSNDTDKRMVLKHFNSITAENEMKPE

SLLAGQTSTGLSYRFSTADAFVDFASTNKIGIRGHTLVWHNQTPDWFFKDSNGQRLSKDALLARLKQYIYDVVGRYKGKVYAWDVVNEA

IDENQPDSYRRSTWYEICGPEYTIEKAFIWAHEADPNAKLFYNDYNTEISKKRDFIYNMVKNLKSKGIPIHGIGMQCHINVNWPSVEIE

NSIKLFSSIPGIEIHITELDMSLYNYGSSENYSTPPQDLLQKQSQKYKEIFTMLKKYKNVVKSVTFWGLKDDYSWLRSFYGKNDWPLLF

FEDYSAKPAYWAVIEASGVTTSSPTPTPTPTVTVTPTPTPTPTPTVTATPTPTPTPVSTPATGGQIKVLYANKETNSTTNTIRPWLKVV

NSGSSSIDLSRVTIRYWYTVDGERAQSAVSDWAQIGASNVTFKFVKLSSSVSGADYYLEIGFKSGAGQLQPGKDTGEIQIRFNKSDWSN

YNQGNDWSWLQSMTSYGENEKVTAYIDGVLVWGQPPSGATPAPTMTVAPTATPTPTLSPTVTPTPAPTQTAIPTPTLTPNPTPTSEIPD

DTNDDWLYVSGNKIVDKDGRPVWLTGINWFGYNTGTNVGDGVWSCNLKDTLAEIANRGFNLLRVPISAELILNWSQGIYPKPNINYYVN

PELEGKNSLEVFDIVVQTCKEVGLKIMLDIHSIKTDAMGHIYPVWYDEKFTPEDFYKACEWITNRYKNDDTIIAFDLKNEPHGKPWQDT

TFAKWDNSTDINNWKYAAETCAKRILNINPNLLIVIEGIEAYPKDDVTWTSKSSSDYYSTWWGGNLRGVRKYPINLGKYQNKVVYSPHD

YGPSVYQQPWFYPGFTKESLLQDCWRPNWAYIMEENIAPLLIGEWGGHLDGADNEKWMKYLRDYIIENHINHTFWCFNANSGDTGGLVG

YDFTTWDEKKYSFLKPALWQDSQGRFVGLDHKRPLGTNGKNINITTYYNNNEPEPVPASK

The following is the amino acid sequence (aa 507-1039) of Csac GH5 including linker and c-terminal residues (SEQ ID NO:3):

MFKSGAGQLQPGKDTGEIQIRFNKSDWSNYNQGNDWSWLQSMTSYGENEKVTAYIDGVLVWGQEPSGATPAPTMTVAPTATPTPTLSPT

VTPTPAPTQTAIPTPTLTPNPTPTSSIPDDTNDDWLYVSGNKIVDKDGRPVWLTGINWFGYNTGTNVFDGVWSCNLKDTLAEIANRGFN

LLRVPISAELILNWSQGTYPKPNINYYVNPELEGKNSLEVFDIVVQTCKEVGLKIMLDIHSIKTDAMGHIYPVWYDEKFTPEDFYKACE

WITNRYKNDDTILAFDLKNEPHGKPWQDTTFAKWDNSTDINNWKYAAETCAKRILNINPNLLIVIEGIEAYPKDDVTWTSKSSSDYYST

WWGGNLRGVRKYPINLGKYQNKVVYSPHDYGPSVYQQPWFYPGFTKESLLQDCWRPNWAYIMEENIAPLLIGEWGGHLDGADNEKWMKY

LRDYIIENHIHHTFWCFNANCGDTGGLVGYDFTTWDEKKYSFLKPALWQDSQGRFVGLDHKRPLGTNGKNINITTYYNNNEPEPVPASK

The following is the amino acid sequence (aa 374-1039) of Csac CBM3-GH5 including linker and c-terminal residues (SEQ ID NO:4):

```
MGVTTSSPTPTPTPTVTVTPTPTPTPTPTVTATPTPTPTPVSTPATGGQIKVLYANKETNSTTNTIRPWLKVVNSGSSSIDLSRVTIRY

WYTVDGERAQSAVSDQAQIGASNVTFKFVKLSSSVSGADYYLEIGFKSGAGQLQPGKDTGEIQIRFNKSDWSNYNQGNDWSWLQSMTSY

GENEKVTAYIDGVLVWGQEPSGATPAPTMTVAPTATPTPTLSPTVTPTPAPTQTAIPTPTLTPNPTPTSSIPDDTNDDWLYVSGNKIVD

KDGRPVWLTGINWFGYNTGTNVFDGVWSCNLKDTLAEIANRGFNLLRVPISAELILNWSQGIYPKPNINYYVNPELEGKNSLEVFDIVV

QTCKEVGLKIMLDIHSIKTDAMGHIYPVWYDEKFTPEDFYKACEWITNRYKNDDTIIAFDLKNEPHGKPWQDTTFAKWDNSTDINNWKY

AAETCAKRILNINPNLLIVIEGIEAYPKDDVTWTSKSSSDYYSTWWGGWLRGVRKYPINLGKYGNKVVYSPHDYGPSVYQQPWFYPGFT

KESLLQDCWRPNWAYIMEENIAPLLIGEWGGHLDGADNEKWMKYLRDYIIENHIHHTFWCFNANSGDTGGLVGYDFTTWDEKKYSPLKP

ALWQDSQGRFVGLDHKRPLGTNGKNINITTYYNNNEPEPVPASK
```

In some embodiments of the invention, the composition further comprises one or more endoglucanase enzymes. In some embodiments of the invention, the one or more endoglucanase enzymes are thermostable or thermophilic endoglucanase enzymes. In some embodiments of the invention, the composition is a hydrolysis cocktail tolerant to high concentrations of IL.

Suitable thermostable or thermophilic endoglucanase enzymes include, but are not limited to, any thermostable cellulase from the genus *Anaerocellu*, *Bacillus*, *Rhodothermus*, *Thermotoga*, *Sulfolobus*, *Pyrococcus*, or *Alicyclobacillus*. Suitable species of the genus *Anaerocellu* include *A. thermophilum*. Suitable species of the genus *Bacillus* include *B. subtilus*. Suitable species of the genus *Rhodothermus* include *R. marinus*. Suitable species of the genus *Thermotoga* include *T. maritima*, *T. neapoltana*, and *T. subterranea*. Suitable species of the genus *Sulfolobus* include *S. solfataricus* MT4, *S. acidocaldarius*, and *S. shibatae*. Suitable species of the genus *Pyrococcus* include *P. horikoshii*, *P. horicoshi*, *P. woesei*, and *P. furiosus*. Suitable species of the genus *Alicyclobacillus* include *A. acidocaldarius*. In some embodiments, the thermostable cellulase is a cellulase obtained from or native to a hyperthermophilic microorganism, an extremophilic microorganism, or thermophilic microorganism. In some embodiments, the thermostable cellulase is a thermophilic cellulase. In some embodiments, the thermostable cellulase is a thermostable endoglucanase or a thermophilic endoglucanase. Some of the suitable thermostable cellulases are listed in Table 1. Suitable thermostable endoglucanases are described in U.S. Patent Provisional Application Ser. Nos. 61/172,653, and PCT International Patent Application No. PCT/US2010/32320, which are hereby incorporated by reference.

The above references are incorporated by reference as though each is individually and specifically incorporated by reference.

Suitable thermostable or thermophilic endoglucanase enzymes also include, but are not limited to, any mutant *Thermotoga maritima* thermostable cellulase with increased cellulase activity. The thermostable cellulase mutant comprises an amino acid sequence having at least 70% identity as compared to the amino acid sequence of wild-type cellulase of *Thermotoga maritima* MSB8 (encoded by the cel5A gene), wherein the amino acid sequence of the thermostable cellulase mutant comprises one or more amino acid residues are altered as compared to the amino acid sequence of the wild-type cellulase. The thermostable cellulase mutant has a cellulase activity higher than that of the wild-type *T. maritima* thermostable cellulase. Such *Thermotoga maritima* thermostable cellulase mutants are taught in U.S. Patent Provisional Application Ser. No. 61/172,668, and PCT International Patent Application No. PCT/US2010/32320, which are hereby incorporated by reference A thermostable cellulase is a cellulase, or a homologous enzyme thereof, that has an enzymatic activity for hydrolyzing cellulose, hemicelluloses, or lignocelluloses that has an optimal temperature that is equal to or more than 65° C. A thermostable cellulase includes, but is not limited to, a endoglucanase, exoglucanase, or β-1,4-D-glucosidase, or a homologous enzyme thereof, that has an optimal temperature that is equal to or more than 65° C. In some embodiments, optimal temperature is equal to or more than 85° C. In some embodiments, optimal temperature is equal to or more than 95° C.

A homologous cellulase is an enzyme that has a polypeptide sequence that is at least 70%, 75%, 80%, 85%, 90%, 95% or 99% identical to any one of the enzymes described

TABLE 1

Source microorganisms and properties of thermostable cellulases.

| Organism | Enzyme properties | | References |
|---|---|---|---|
| | Optimal temperature (° C.) | Optimal pH | |
| *Anaerocellu thermophilum* | 85-90 | 5.0-6.6 | Zverlev et al. (1998) |
| *Bacillus subtilis* | 65-70 | 5.0-6.5 | Mawadza et al. (2000) |
| *Pyrococcus furiosus* | 102-105 | — | Kengen et al. (1993) |
| *Pyrococcus horicoshi* | 97 | — | Ando et al. (2002) |
| *Rhodothermus marinus* | 95 | 6.5-8.0 | Hreggvidsson et al. (1996) |
| *Thermotoga maritima* MSB8 | 95 | 6.0-7.0 | Bronnenmeier et al. (1995) |
| *Thermotoga neapoltana* (EndocellulaseA) | 95 | 6.0 | Bok et al. (1998) |
| *Thermotoga neapoltana* (EndocellulaseB) | 106 | 6.0-6.6 | Bok et al. (1998) | in U.S. Patent Provisional Application Ser. Nos. 61/172,653 and 61/172,668, and PCT Interntional Patent Application No. PCT/US2010/32320, which are hereby incorporated by reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

Ionic liquid (IL)

In some embodiments, the composition further comprises a suitable ionic liquid (IL). The suitable IL used in the present invention can be any IL suitable for pretreatment of biomass and for the hydrolysis of cellulose by the CBH of the present invention. Suitable IL are taught in ChemFiles (2006) 6 (9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Such suitable IL include, but are limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl$_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris(2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, and the like. The ionic liquid can comprises one or a mixture of the compounds. Further IL are taught in U.S. Pat. No. 6,177,575, which is incorporated by reference.

The ionic liquid is of a concentration of more than 0% of the composition or solution. In some embodiments, the concentration of IL is equal to or more than 1%, equal to or more than 2%, equal to or more than 3%, equal to or more than 5%, equal to or more than 10%, equal to or more than 15%, or equal to or more than 20%.

In some embodiments of the invention, the IL has a concentration from more than 0% to about 50%. In some embodiments of the invention, the IL has a concentration from more than 0% to about 35%. In some embodiments of the invention, the IL has a concentration from more than 0% to about 20%. In some embodiments of the invention, the IL has a concentration from about 5% to about 20%.

The present invention provides for a composition comprising an ionic liquid and a polypeptide comprising the amino acid sequence of Csac GH5 and having a CBH or exoglucanase activity. In some embodiments, the composition further comprises a cellulose, wherein the polypeptide is capable of hydrolyzing the cellulose. In some embodiments, the composition comprises a pretreatment biomass.

METHODS OF THE PRESENT INVENTION

The present invention provides for a method of hydrolyzing a cellulose, comprising: (a) providing a composition comprising a solution comprising an ionic liquid and a cellulose, and (b) introducing a polypeptide comprising the amino acid sequence of Csac GH5 and having a CBH or exoglucanase activity to the solution, such that the cellulose is hydrolyzed by the polypeptide. In some embodiments, the solution comprises a pretreatment biomass comprising the cellulose.

In some embodiments, the pretreatment biomass is a pretreatment cellulose biomass, pretreatment hemicellulose biomass, pretreatment lingo-cellulose biomass, or a mixture thereof.

The present invention provides for a method for converting lignocellulosic biomass to sugars for the production of biofuels. Methods for the pretreatment of biomass and the downstream enzymatic hydrolysis that is required to breakdown the long polymers of cellulose to simpler sugars for biofuels production.

The present invention provides for a method that is compatible with biomass pretreatment with IL.

In some embodiments, the method results in essentially the 100% hydrolysis of cellulose to glucose. In some embodiments, the method results in the 90% hydrolysis of cellulose to glucose. In some embodiments, the method results in the 80% hydrolysis of cellulose to glucose. In some embodiments, the method results in the 50% hydrolysis of cellulose to glucose.

Biomass Pretreatment

Biomass or cellulose pretreatment is described in Hermanutz, et al. (2008) *Macromol. Symp.* 262:23-27, which is incorporated by reference.

The present invention addresses two significant challenges in biomass processing—IL have shown to be very effective in "solubilizing" lignocellulosic biomass. While the solubilized components of biomass—cellulose, hemicellulose and lignin—can be separated by the addition of solvents, it is inherently expensive and time consuming additional step. The discovery of enzymes that tolerate high concentrations of IL can make the process more cost effective in two ways—first, the enzymes can be used directly in the solution of IL and biomass to produce sugars from cellulose; and second, if the cellulose is "crashed out", that is, precipitated from the solution using antisolvents like water and ethanol, with a resulting carryover of the IL, then the enzymes can be used to solubilize the cellulosic sugars without need for further washing to remove the IL.

The current method for biomass pretreatment is a two-step process: first step of chemical pretreatment of biomass which is incompatible with the second-step—downstream enzyme hydrolysis. The characteristics of the pretreated biomass like pH and temperature have to be modified so that fungal enzymes, the industrial standard enzymes for hydrolyzing cellulosic sugars, are not compatible with either the temperature or the pH of the solution. This additional step adds time and cost to the overall process. We have shown a method whereby an efficient method of hydrolyzing cellulosic sugars—using extremophilic enzymes—is compatible with an efficient method for pretreating biomass using ionic liquids.

The present invention provides for an enzyme for exoglucanase, or cellobiohydrolase, that can cleave a cellulose polymer in a processive manner releasing cellobiose units from the cellulose polymer. The CBH of the present invention can be used in concert with an endoglucanase to improve the kinetics and the efficiency of hydrolysis of a cellulose polymer.

Applications

The present invention can be used in the hydrolysis of pretreated biomass for the production of sugars from biomass. The sugars can be used in all process that use C6 sugars, such as glucose, as the enzymes and the process has shown to hydrolyze cellulose sugars and the resulting sugars can be used for any intended purpose. The process is of significant interest in biomass processing or biofuels and other biomaterials, paper recycling and pulp processing for paper manufacturing.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

A Hyperthermophilic Cellobiohydrolase from *Caldicellulosiruptor saccharolyticus*

CBH is a modular cellulolytic gene from a hyperthermophilic and anaerobic bacterium *Caldicellulosiruptor saccharolyticus* (*C. Sac*), which contains the glycoside hydrolase family 10 (GH10), carbohydrate binding module family 3 (CBM3), and glycoside hydrolase family 5 (GH5) domains in a single open reading frame (ORF). We have expressed, purified, and characterized the function of the recombinant GH5 with and without CBM3 domain. The nucleotide sequence of the ORF is codon-optimized and then synthesized for protein expression in *E. coli*. The translated products contain c-terminal V5 epitope and His (×6) tags from the pDEST42 vector sequence. The recombinant proteins CBM3-GH5 and GH5 are expressed in BL21(DE3)Star *E. coli* and purified by affinity (HisTrap FF) and ion-exchange (HiTrap Q) chromatography methods. The average yields are 4 mg and 3 mg per liter, respectively. The result of the analysis is shown in Table 2.

TABLE 2

| Construct (see FIG. 1) | Protein expression (soluble) | CMCase activity | CBH activity (cellobiohydrolase or exoglucanase) |
| --- | --- | --- | --- |
| A | +/− | Yes | Not determined |
| B | − | No | No |
| C | ++ | Yes | Yes |
| D | − | No | No |
| E | +++ | Yes | Yes |

Figure 2:
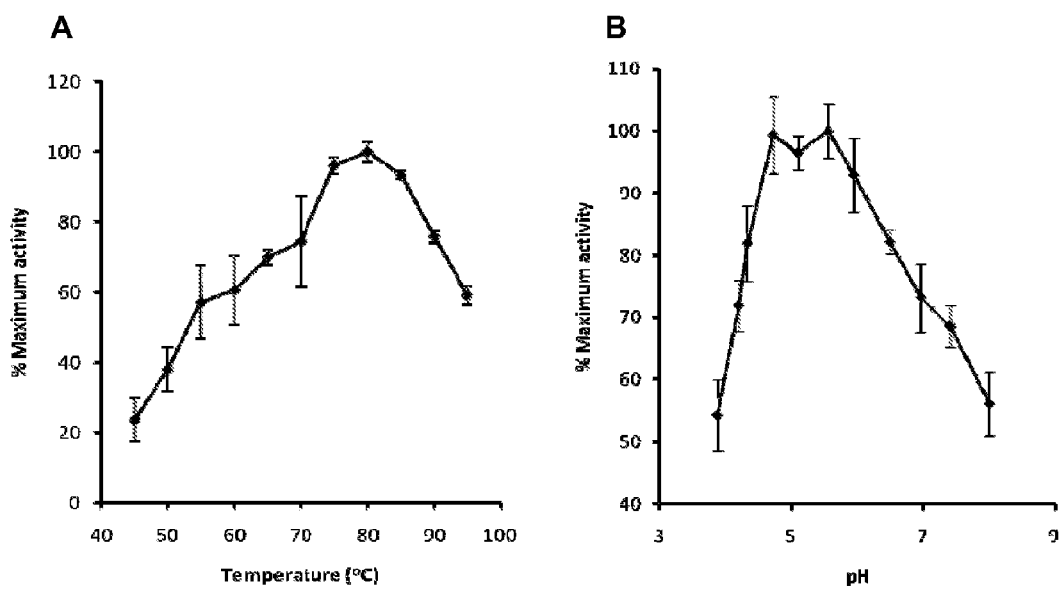
FIG. 2 shows the temperature and pH dependent activity of Csac GH5. Panel A shows the temperature dependent activity of Csac GH5. Panel B shows the pH dependent activity of Csac GH5.

To determine the optimum conditions for the enzymatic activity of GH5 on CMC under different pH and temperature ranges was measured by DNS assay. The maximum activity is observed at 80° C. and at pH between 4.7 and 5.5; the optimum conditions of the GH5 activity on CMC is at a higher temperature and at a lower pH than the optimum growth conditions of *C. sac* (70° C., at neutral pH). See FIG. 2. In addition, Csac GH5 is also active on 4-nitrophenyl β-D-cellobioside, but not active on 4-nitrophenyl β-D-glucopyranoside (up to 1 hr incubation). Therefore, GH5 is a cellobiohydrolase/exoglucanase that produces cellobiose.

Figure 3:
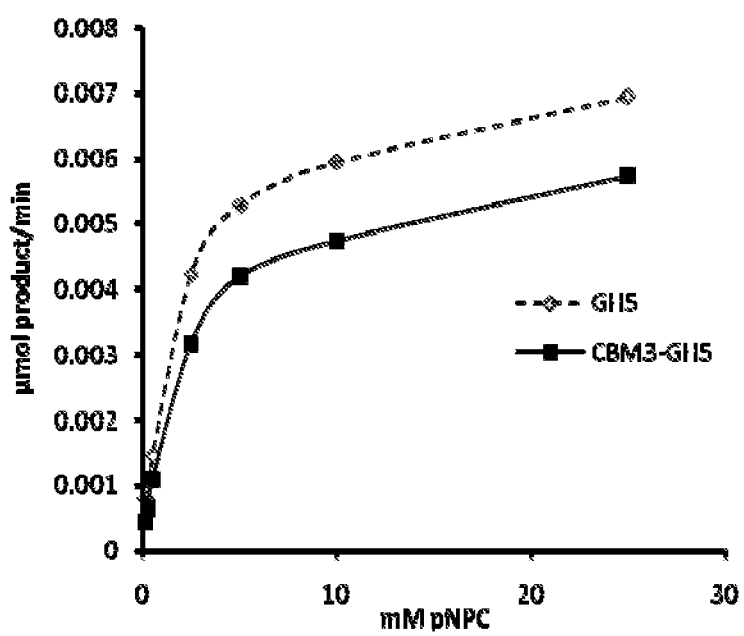
FIG. 3 shows the influence of the CBM3 domain on the catalytic activity of Csac GH5.

To examine the catalytic activity of GH5 in detail, the hydrolysis of nitrophenol from 4-nitrophenyl-β-D-cellobioside (pNPC) and 4-nitrophenyl-β-D-glucopyranoside (pNPG) are measured. Under the optimum reaction condition that is previously found (80° C. and pH 5.5), pNPC was hydrolyzed by both CBM3-GH5 and GH5. However, pNPG is not hydrolyzed up to one hour under the same condition. See FIG. 3. These results suggest that the GH5 domain of C. sac is a hyperthermophilic cellobiohydrolase that lacks the β-glucosidase activity. The product inhibition by cellobiose is examined by adding unlabeled cellobiose into reaction mixtures containing 5 mM of pNPC. The $IC_{50}$ inhibition constant for cellobiose on the catalytic activity of GH5 is found at c.a. 30 mM. The kinetics of pNPC hydrolysis by CBM3-GH5 and GH5 are compared to see whether the CBM3 domain can influence the catalytic activity of the GH5 domain on a soluble substrate. The kinetic parameters are determined by Eadie-Hofstee plots ($V_{max}$, for CBM3-GH5: 0.71 μmol/min/mg; GH5: 0.62 0.71 μmol/min/mg). $K_m$ and $k_{cat}$ values are similar between CBM3-GH5 ($K_m$ at 2.2 mM and $k_{cat}$ at 46 $min^{-1}$) and GH5 ($K_m$ at 2.4 mM and $k_{cat}$ at 49 $min^{-1}$). Thus, the CBM3 domain does not have any significant effect on the hydrolysis of the soluble substrate pNPC by the GH5 domain.

Figure 4:
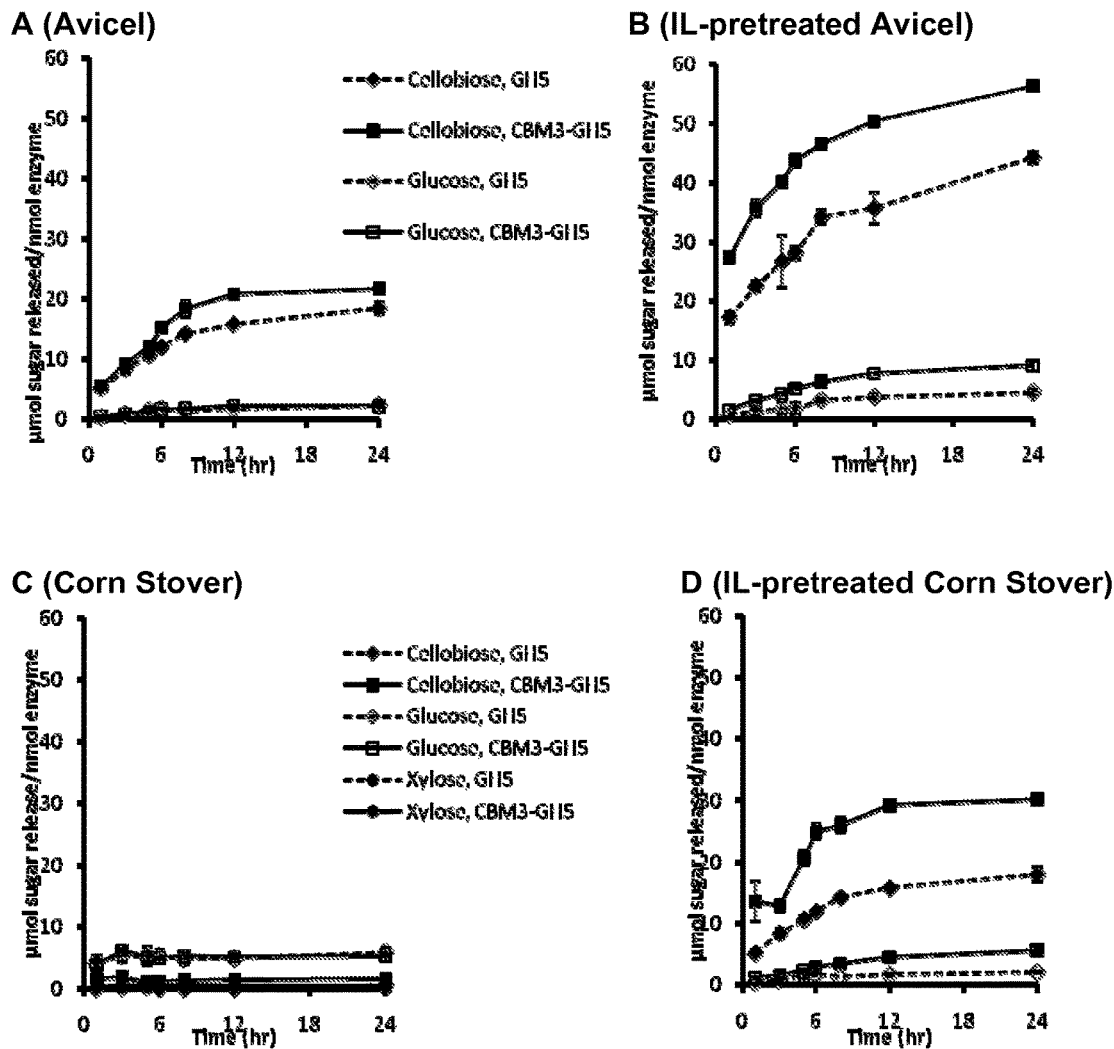
FIG. 4 shows the cellobiose production from insoluble substrates by CBM3-GH5 and GH5. Panel A shows the sugar released from Avicel. Panel B shows the sugar released from IL-pretreated Avicel. Panel C shows the sugar released from corn stover. Panel D shows the sugar released from IL-pretreated corn stover. The solid diamonds correspond to the data for cellobiose, GH5. The solid squares correspond to the data for cellobiose, CBM3-GH5. The open diamonds correspond to the data for glucose, GH5. The open squares correspond to the data for glucose, CBM3-GH5. The solid circles correspond to the data for cellobiose, GH5. The solid circles correspond to the data for cellobiose, CBM3-GH5.

The effect of CBM3 on the cellobiohydrolase activity on solid substrates by GH5 is tested on Avicel and corn stover. These solid substrates are pretreated with the ionic liquid 1-ethyl-3-methylmidazolium acetate ([C2mim][OAc]). The analysis of products by high-performance anion-exchange chromatography (HPAEC) show that cellobiose is the predominant sugar released from solid substrates by CBM3-GH5 and GH5, except from the untreated corn stover. See FIG. 4. Enzyme digestion is performed by mixing 30 mg of substrate and 10 μg of protein in 0.5 mL volume and incubating at 80° C. and pH 5.5 for 17 hours. GH5 and CBM3-GH5 are able to produce more cellobiose and glucose from pre-treated Avicel than untreated Avicel. These results confirm that GH5 is indeed a cellobiohydrolase. Interestingly, even though the β-glucosidase activity is not detected from pNPG assay, a significant amount of glucose is also released from the pretreated solid substrates by enzymatic hydrolysis.

In conclusion, the GH5 domain from CsacF7 is a cellobiohydrolase based on enzyme assays on soluble substrates ($T_{op}$ at 80° C., and $pH_{op}$ between 4.5 and 5.5). This result demonstrates that Saul et al. (1990) disclosure that GH10 is a cellobiohydrolase domain is in error. Both CBM3-GH5 and GH5 produced cellobiose from Avicel and pretreated corn stover. CBM3-GH5 produced more cellobiose than GH5 did from insoluble substrates (Avicel and IL-pretreated corn stover), but not from the tested soluble substrates (pNPC).

Figure 5:
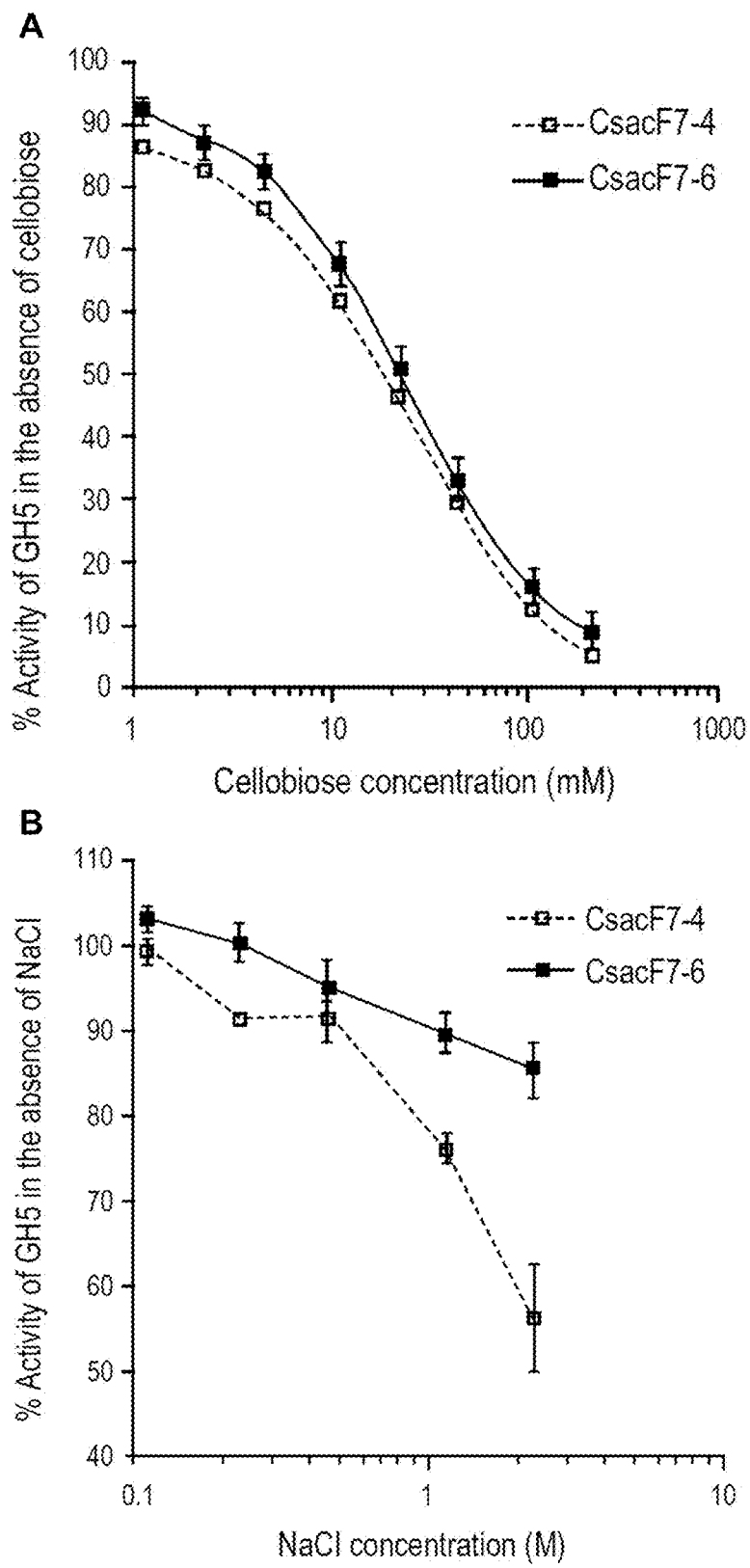
FIG. 5 shows the influence of product and ionic strength on CBH activity. Panels A and B show the effect of cellobiose and NaCl concentration, respectively, on CBH activity. CsacF7-4 and CsacF7-6 indicate GH5 and CBM3-GH5, respectively. The data points for CsacF7-4 and CsacF7-6 are represented by open diamonds and solid squares, respectively.

GH5 and CBM3-GH5 (constructs C and E, respectively) are tested to determine the influence of product and ionic strength on CBH activity. See FIG. 5. Results indicate that CBH activity is inhibited by cellobiose with $IC_{50}$ of ca. 30 mM, and that at least 80% residual CBH activity is observed for CBM3-GH5 at 2.3 M NaCl.

Figure 6:
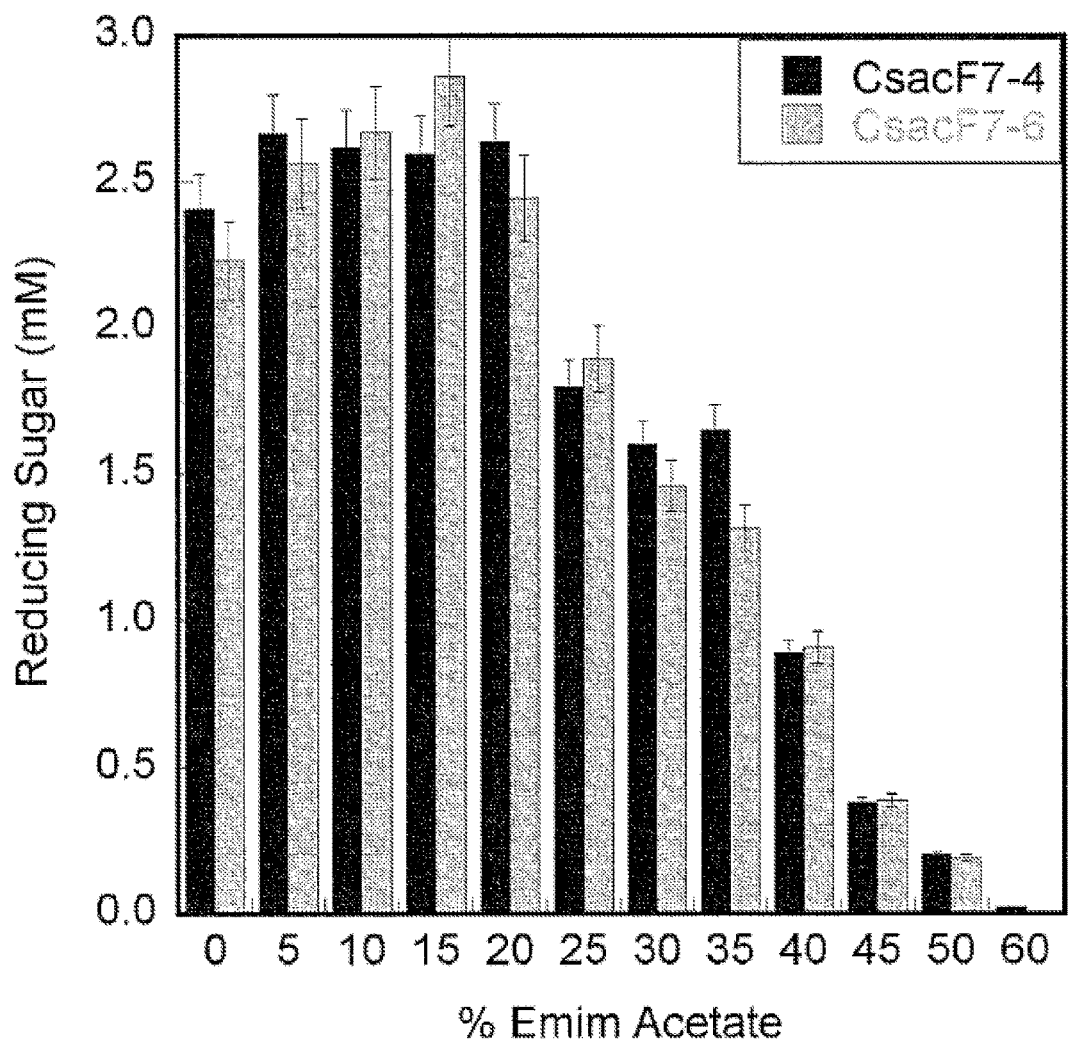
FIG. 6 shows the influence of IL on CBH activity of Csac CBH. CsacF7-4 and CsacF7-6 indicate GH5 and CBM3-GH5, respectively.

GH5 and CBM3-GH5 (constructs C and E, respectively) are tested to determine the effect of IL concentration on the CBH activity of GH5. Carboxymethyl cellulose (CMC) is used as the substrate for the enzymatic reaction, and the amount of released products containing reducing ends is measured by DNS. The results are shown in FIG. 6. The CBH activity remains fairly highly from 0% to more than 20% EMIM acetate. From 25% EMIM acetate the CBH activity starts to decrease and the CBH activity diminished at about 60% EMIM acetate.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising (a) a polypeptide comprising a first amino acid sequence comprising the amino acid sequence of amino acids 636-975 of *Caldicellulosiruptor saccharolyticus* ("Csac") cellobiohydrolase (CBH) wherein said first amino acid sequence has a thermostable or thermophilic CBH or exoglucanase activity and the Csac CBH has the amino acid sequence of SEQ ID NO:2; and (b) more than 0% to 50% of an ionic liquid ("IL").

2. The composition of claim 1, wherein the polypeptide further comprises a second amino acid sequence having at least 90% identity with the amino acid sequence of amino acids 424-506 of SEQ ID NO:2 (carbohydrate binding module family 3 (CBM3)) wherein said second amino acid sequence is capable of binding a carbohydrate.

3. The composition of claim 2, wherein the carbohydrate is a cellulose.

4. The composition of claim 3, wherein the composition further comprises a cellulose capable of being cleaved by a Csac glycoside hydrolase family 5 (GH5) to produce a cellobiose.

5. The composition of claim 1, wherein the composition has a temperature of at least 65° C.

6. The composition of claim 5, wherein the composition has a temperature of at least 80° C.

7. The composition of claim 1, wherein the composition has a pH from 4.7 to 5,5.

8. The composition of claim 1, wherein the composition comprises more than 0% to 35% of the ionic liquid ("IL").

9. The composition of claim 2, wherein the second amino acid sequence has at least 95% identity with amino acids 424-506 of SEQ ID NO:2.

10. The composition of claim 9, wherein the second amino acid sequence has at least 99% identity with amino acids 424-506 of SEQ ID NO:2.

11. The composition of claim 10, wherein the second amino acid sequence comprises amino acids 424-506 of SEQ ID NO:2.

12. The composition of claim 1, wherein the composition further comprises one or more thermostable or thermophilic endoglucanase enzymes.

13. A method of hydrolyzing a cellulose, comprising: (a) providing a composition comprising a solution comprising more than 0% to 50% of an ionic liquid ("IL") and a cellulose, and (b) introducing a polypeptide comprising an amino acid sequence comprising the amino acid sequence of amino acids 636-975 of *Caldicellulosiruptor saccharolyticus* ("Csac") cellobiohydrolase (CBH) wherein said amino acid sequence has a thermostable or thermophilic CBH or exoglucanase activity and the Csac CBH has the amino acid sequence of SEQ ID NO:2, such that the cellulose is hydrolyzed by the polypeptide.

14. The method of claim 13 wherein the solution comprises a pretreatment biomass comprising the cellulose.

15. The method of claim 14, wherein the pretreatment biomass is a pretreatment cellulose biomass, pretreatment hemicellulose biomass, pretreatment lingo-cellulose biomass, or a mixture thereof.

16. The method of claim 13, wherein the IL is 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, or 1-alkyl-3-alkylimidazolium halide, wherein an "alkyl" is an alkyl group comprising from 1 to 10 carbon atoms, and an "alkanate" is an alkanate comprising from 1 to 10 carbon atoms.

17. The method of claim 13, wherein the IL is 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AlCl_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris (2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, or choline salicylate.

18. The method of claim 13, wherein the IL comprises a concentration equal to or more than 1% of the solution.

19. The method of claim 18, wherein the IL comprises a concentration equal to or more than 5% of the solution.

20. The method of claim 19, wherein the IL comprises a concentration equal to or more than 10% of the solution.

21. The method of claim 20, wherein the IL comprises a concentration equal to or more than 20% of the solution.

22. The method of claim 1, wherein the solution has a temperature of at least 65° C.

23. The method of claim 22, wherein the solution has a temperature of at least 80° C.

24. The method of claim 1, wherein the solution has a pH from 4.7 to 5.5.

25. The composition of claim 1, wherein the concentration of IL in the composition is equal to or more than 1%.

26. The composition of claim 25, wherein the concentration of IL in the composition is equal to or more than 10%.

27. The composition of claim 1, wherein the IL is 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, or 1-alkyl-3-alkylimidazolium halide, wherein an "alkyl" is an alkyl group comprising from 1 to 10 carbon atoms, and an "alkanate" is an alkanate comprising from 1 to 10 carbon atoms.

28. The composition of claim 1, wherein the IL is 1-ethyl-3-methylimidazolium acetate (EMIN Acetate), 1-ethyl-3-methylimidazolium chloride (EMIN Cl), 1-ethyl 3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl$_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris (2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, or choline salicylate.

29. The composition of claim 1, wherein the polypeptide further comprises a C-terminal tag.

30. The composition of claim 29, wherein the C-terminal tag is a V5 epitope tag or a His tag.

\* \* \* \* \*